(12) United States Patent
Jesenko et al.

(10) Patent No.: US 9,563,954 B2
(45) Date of Patent: Feb. 7, 2017

(54) METHOD FOR CAPTURING THE THREE-DIMENSIONAL SURFACE GEOMETRY OF OBJECTS

(71) Applicant: a.tron3d GmbH, Klagenfurt am Worthersee (AT)

(72) Inventors: Jurgen Jesenko, Finkenstein (AT); Andreas Blassnig, Klagenfurt (AT); Helmut Angerer, Klagenfurt (AT)

(73) Assignee: a.tron3d GmbH, Klagenfurt am Wörthersee (AT)

( * ) Notice: Subject to any disclaimer, the term of this patent is extended or adjusted under 35 U.S.C. 154(b) by 106 days.

(21) Appl. No.: 14/579,470

(22) Filed: Dec. 22, 2014

(65) Prior Publication Data
US 2015/0178908 A1 Jun. 25, 2015

(30) Foreign Application Priority Data
Dec. 23, 2013 (EP) .................................... 13450056

(51) Int. Cl.
*G06T 7/00* (2006.01)
*G06T 19/20* (2011.01)
(Continued)

(52) U.S. Cl.
CPC ............. *G06T 7/003* (2013.01); *A61B 5/0088* (2013.01); *A61C 19/04* (2013.01); *G06T 19/20* (2013.01);
(Continued)

(58) Field of Classification Search
CPC ........ G06T 7/0024; G06T 7/003; G06T 7/004; G06T 7/0044; G06T 7/0046; G06T 17/00; G06T 17/05; G06T 2207/10028; G06T 2207/30036; G06T 2219/004
See application file for complete search history.

(56) References Cited

U.S. PATENT DOCUMENTS

2007/0058829 A1* 3/2007 Unal et al. .................... 381/329
2008/0152191 A1* 6/2008 Fujimura et al. ............. 382/103
(Continued)

FOREIGN PATENT DOCUMENTS

WO WO 2011/041812 A1 * 4/2011 ............... G06T 7/00

OTHER PUBLICATIONS

Neubauer et al., "Cell-Based First-Hit Ray Casting", Proc. Symp. on Data Visualization, May 2002, pp. 77-86.*
(Continued)

*Primary Examiner* — Andrew W Johns
(74) *Attorney, Agent, or Firm* — Young & Thompson (57) ABSTRACT

The invention relates to a method for more effectively capturing the three-dimensional surface geometry of objects, particularly for teeth and/or intraoral structures, such as when a scanning processing is interrupted. Depth images are created in which the spatial relationships of points of the depth images to one another remain constant, but an overall spatial orientation of each new depth image is different. Points of the depth image that fulfill a first attribute is verified for every pose. The number of points that have this attribute is then counted. The pose that accordingly has the highest count is thus chosen, and an artificial depth image is then generated, in which the ascertained pose is applied "backwards" to create an artificial depth image. The real new depth image can then be transferred into the artificial depth image in order to create a new pose, which may then be verified by computation.

9 Claims, 4 Drawing Sheets

(51) Int. Cl.
*A61C 19/04* (2006.01)
*A61B 5/00* (2006.01)

(52) U.S. Cl.
CPC ............... *G06T 2207/10028* (2013.01); *G06T 2207/30036* (2013.01)

(56) References Cited

U.S. PATENT DOCUMENTS

| | | | | |
|---|---|---|---|---|
| 2009/0074238 A1* | 3/2009 | Pfister et al. | ................. | 382/100 |
| 2012/0218389 A1* | 8/2012 | Nowak et al. | ................. | 348/47 |
| 2015/0009214 A1* | 1/2015 | Lee et al. | ................. | G06T 17/10 |
| | | | | 345/420 |
| 2015/0145957 A1* | 5/2015 | Son et al. | .......... | H04N 13/0275 |
| | | | | 348/46 |
| 2015/0228114 A1* | 8/2015 | Shapira et al. | ......... | G06T 17/10 |
| | | | | 345/421 |

OTHER PUBLICATIONS

Frisken et al., "Efficient Estimation of 3D Euclidean Distance Fields from 2D Range Images", Proc. IEEE/ACM SIGGRAPH Symp.on Volume Visualization and Graphics, Oct. 2002, pp. 81-88.*
Newcombe et al., "KinectFusion: Real-Time Dense Surface Mapping and Tracking", Proc. 10th IEEE Int'l Symp. on Mixed and Augmented Reality, Oct. 2011, pp. 127-136.*

* cited by examiner

METHOD FOR CAPTURING THE THREE-DIMENSIONAL SURFACE GEOMETRY OF OBJECTS

FIELD OF THE INVENTION

The invention relates to a method for capturing the three-dimensional surface geometry of objects, in particular teeth and/or intraoral structures.

BACKGROUND OF THE INVENTION

Various forms of intraoral scanners, with which depth images of three-dimensional surface geometries can be gained and then merged in different ways, are known from the state of the art. If, however, the process of scanning is interrupted, various elaborate procedures which frequently require human support become necessary in order to resume an interrupted scanning process. Known automated systems are generally unsuccessful or can only function if the area in which the scan is to be applied "anew" has previously been manually restricted.

SUMMARY OF THE INVENTION

The underlying goal of the invention, therefore, is to overcome the shortcomings described above.

This task is solved by the invention by means of a method as initially described, in which the following steps are performed:
1) Loading an available TSDF from a storage medium;
2) Capturing a new depth image;
3) Loading available poses to the loaded TSDF;
4) Applying the loaded poses to the loaded TSDF;
   a) Verifying for each point of the depth image which has been transformed by applying the loaded pose, whether the point has a first defined attribute due to the applied pose and, if applicable, labeling of the point;
   b) Counting all labeled points in the depth image for each pose;
5) Preferential selection of the pose which leads to the most labeled points;
6) Generation of an artificial depth image from the TSDF by means of the selected pose;
7) Application of an ICP method to the new depth image and the artificial depth image to gain a new pose;
8) Verifying whether the ICP method from Step 7 leads to a successful registration;
9) If Step 8 is successful, updating of the existing TSDF by means of the new depth image and the pose gained in Step 7;
10) If Step 8 is unsuccessful, repetition of the steps beginning with Step 4.

In this context, a TSDF is the employed form of notation of the three-dimensional data.

The new depth image can be acquired by any means established by the state of the art.

Poses are geometrical transformations created by folding depth images into one another by means of ICP methods. From every depth image which contributes or has contributed to a TSDF, a pose is generally created in the course of the ICP method. These poses are preferably saved in addition to the distance values normally deposited in a TSDF and recalled over the course of the process of the invention. The order of Steps 1) through 3) as well as any potentially occurring sub-steps is irrelevant to the functionality of the invention. These steps are preferably performed simultaneously, but can also be performed in any desired order.

By applying the loaded poses to the new depth image, depth images are created in which the spatial relationships of the points of the depth images to one another remain constant, but the overall spatial orientation of each new depth image is different. Thus, which points of the depth image fulfill a first attribute can be verified according to the invention for every pose. This attribute is preferably that points of the depth image, should they be noted in the TSDF, are located near the surface previously noted in the TSDF. One can, call this attribute "near surface," for example.

According to the invention, the number of points that have this attribute is then counted. The pose that accordingly has the highest count can thus be chosen.

Ideally, this pose is suitable for noting the new depth image in the TSDF. Realistically, ascertaining a pose with 100% correspondence represents a highly unlikely coincidence. Using the ascertained pose directly would therefore rather falsify the surface noted in the TSDF. Therefore, an artificial depth image is generated in the next step, in which the ascertained pose is applied "backwards", to put it in simplified terms, to the TSDF in order to create an artificial depth image by means of the pose from the TSDF. The real new depth image can then be transferred into the artificial depth image in a further step by means of the intrinsically familiar ICP method. A new pose is thereby created.

Since the artificial depth image originates from the loaded TSDF, the depth image can be inserted into the TSDF with the thereby determined additional pose. It is therefore attempted to register the depth image in the TSDF.

To avoid mistakes in doing so and to achieve the highest possible degree of accuracy, it is additionally assessed whether the registration is valid and successful, respectively. A registration is considered valid if the values newly deposited in the TSDF correspond to the previous values of the TSDF.

If the registration was successful, the scan was resumed and can be continued.

If the registration was not successful, poses again have to be tested according to the steps described above.

In accordance with a preferred further development of the invention, step

3.1) Generation of artificial poses in addition to the existing poses and loading of the artificial poses can take place before step 4), where the generation of artificial poses takes place by applying geometric operations to the existing poses.

This is particularly advantageous if the available poses are very different from the current orientation of the scanner. This can occur, for example, if the scan breaks off after half of the arch of the jaw and an attempt is then made to resume the scan with a scanner rotated by 180°, or if the scan is to be resumed at a slightly different distance after breaking off. Artificial poses are therefore created by applying geometrical operations to the available poses. Thus poses can for example be rotated, tilted toward the object, or moved closer or further away.

Particularly after lengthy, possibly intentional interruptions of the scan, artificial poses will almost always be helpful in arriving at a valid registration. Without artificial poses a successful resumption can be achieved mainly for brief (unintended) interruptions, since the scanner will then usually be in a similar position as before the interruption.

In accordance with a preferred further development of the invention step 1.1) Providing bricks of the loaded TSDF can take place after Step 1).

The TSDF, or alternately a grid of the TSDF, is thereby divided into smaller "sub-grids," known as bricks. These are preferably cube-shaped and especially preferably have sides of length $2^n$.

The bricks can either be loaded with the TSDF or also be generated only as required by dividing the TSDF into smaller subgrids.

In accordance with a preferred further development of the invention step 1.2) Determining which of the provided bricks fulfill a second attribute and marking of these bricks, can take place after Step 1.1).

To this end, every brick is preferably tested, to determine whether there are voxels of the TSDF in the brick which fulfill the first defined attribute. Each brick which contains at least one voxel with the first attribute is marked with the second defined characteristic.

Once this has taken place, the process can be accelerated by means of an especially preferred further development of the invention, in which, once Step 1.2) has taken place, step 4)a.1) Testing for each point of the depth image which has been transformed by applying the loaded pose, whether the point, due to the applied pose, lies within a brick with the second defined attribute, and, in the affirmative case, marking of the point then takes place instead of Step 4)a).

Thus the process can, depending on the chosen size of the brick, be implemented far more quickly than with Step 4)a), since verification is much coarser.

The apparent disadvantage that a pose determined by one of the following steps could possibly be less precise is completely avoided, as described above, by Steps 6) through 10), since it is already assumed that the determined pose is not "perfect."

BRIEF DESCRIPTION OF THE DRAWINGS

Hereafter, an intraoral scanner operated by means of a process in accordance with the invention will serve as an example and be described more comprehensively and in further detail with reference to the illustrations.

The illustrations show:

FIG. 2 a schematized depiction of the cone of vision of a camera in relation to a brick, FIG. 3 a schematized comparison between the normals in a volume model of the TSDF and the surface normal in a depth image, FIG. 4 a graph showing a weighting function of the weighting values of the voxels of the TSDF FIG. 5 a schematized depiction of a scanner head with a simplified scanner volume which is arranged within the scanner head, and FIG. 6 a comparison between points of a depth image which are transformed with two different poses and compared with a number of bricks

DETAILED DESCRIPTION OF THE INVENTION

In principle, an intraoral scanner which is to be operated according to the process defined by the invention can be constructed from two essential main components: a handpiece which features internally or externally recorded firmware and an arithmetic unit, particularly a computer, which possesses appropriate software.

The computer can be a commercially available computer in which the software is merely installed, or for example a specialized device which can only perform dental tasks. The former has the advantage that such a system can be applied without particular logistical effort anywhere where at least a mobile computer, such as a laptop, is available. The latter has the advantage that a computer designed entirely for dental tasks can be furnished with particularly appropriate hardware, such as special graphics cards, and can therefore scan more quickly under certain circumstances.

In this process, the firmware assumes various tasks. Among other things, it can ensure, for example, that stereo images are recorded synchronously in a stereometric system. The firmware can also include sensor parameterization, control USB data transfer (for instance for video images or parameterization, status and measurement data), read sensors (for instance temperature of projector LEDs, data from position sensors, keyboard events) and drive feedback elements (for instance multicolored status LEDs).

The computer's software includes, as an example, the following software modules:

a communication module, for example a USB driver module, which acts as a data interface between the handpiece and the computer, a controller module which primarily reads and controls the physical processes during scanning, in particular bidirectional data transfer, i.e. synchronous pairs of video images, exposure time and amplification, projector LED temperature (and optionally other temperature values), data from position sensors, various states of the status LED (for example "red," "yellow," and "green"), events triggered by keys on the handpiece (keyboard events), calibration data of the stereocamera, and parameters for individual PC software modules;

a measurement module which converts the acquired data into three-dimensional data. For this purpose, an $S^3E$ system, for example, can be used which is based on a camera/camera and/or camera/projector setup; where required, this module can also contain means of improving the acquired data. These means can for example include data to lens errors with which the exposures can be rectified or data regarding the dark frame, with which the dark current can be compensated.

A scanning procedure described in a simplified manner exhibits the following steps:

projection of a light pattern onto the surface of teeth and gums, synchronous (if required) recording of pairs of stereo images, whereas stereo pair does not necessarily have to be composed of two two-dimensional images. A pair comprised of projection data and one image is also conceivable.

analysis and processing of the data by means of the arithmetic unit.

If available, the USB connection can also take on the power supply of the handpiece.

Hereafter, the $S^3E$, which is a preferred form of implementation of the measurement module, will be explained.

In a 3D survey of a scene with a measurement module in the form of a $S^3E$ system, at least two cameras and a light pattern projector with a light pattern which is known beforehand are necessary. From this setup the 3D survey of a scene can be performed—independently both by a pair of cameras as well as a camera image together with a deposited according light pattern. The 3D data are transformed into one another and in sum thereby each provides a denser 3D data set thanks to their different perspectives, in other words, more information per real surface unit of the object. The two camera positions or the positions of one of the cameras and the projector, respectively, relative to the scene must be different. The distance between two cameras or a camera and the projector, respectively, is called the stereo base. The cameras and the projector are geometrically described by means of a pinhole camera model; individual camera coordinate systems and a projector coordinate system are spanned in the respective foci (=perspectival projection center). The z-axes (=optical axis) of the camera coordinate systems are aligned so that these are normal to the respective image planes. The position and orientation of the coordinate systems in relation to one another must be calibrated (i.e. known) in order to be able to triangulate the 3D coordinates of the respective point in space in one of the camera coordinate systems via individual corresponding areas in the respective stereo image pairs or via camera image and projection pattern (and the known spatial position of the foci respective to one another). Image defects caused by physical optical lenses (such as a distortion of the image, lense flaws or the like) are measured and mathematically compensated. The parameterization of the mathematical model occurs as part of the calibration process. With a camera image pair and an image of a (known) projection pattern, a 3D reconstruction of the particular section of a scene is possible, in which ideally the coordinates of the respective point in space can be calculated for each corresponding pair of points. Based on the underlying measurement principle, no additional light pattern source is needed for the stereo measurement process with two cameras, since in theory identical spots of the object can be recognized and measured between two images of an image pair even without an artificial pattern. According to the invention, the projection of a (static) random light pattern is utilized in order to be able to extract the respective corresponding image points in as stable a manner and as unambiguously as possible given non-textured or faintly textured tooth surfaces. Additionally, the 3D reconstruction by means of the camera/projector setup can also thus be implemented. In addition, the projection also serves as illumination. Finding correspondences (identification of point pairs, that is, points which show the same spot on the object to be seen in both images of the stereo image pair) in stereo image pairs is, in principle, performed by means of the analysis of the image point proximity of each individual image point and is done with a precision of fractions of a pixel (sub-pixel accuracy). This can be done, for example, as described in WO 2011/041812 A1. It contains, in addition, slanted correlation elements to compensate the perspective distortion of the camera images and is calculated for several different resolution levels. The resulting measurement accuracy of the system is determined to a large extent by the quality of the calibration of the cameras with one another and the calibration of the projector with the camera and the reliability of finding correspondences as described above.

The starting point of the creation of a 3D model is an initial depth image which is gained, for example, through at least one of the methods mentioned above. This initial depth image defines the origin of a world coordinate system. It is entirely irrelevant where exactly on the object to be recorded (or also at which spot on the arch of the jaw) the scan is begun. In standard operation the measurement software then provides the current depth image as well as a translation vector and a rotation matrix, in order to fit this depth image into a global model. In this context, the global model is the entirety of the previously acquired virtual surface geometry. The position of a virtual camera moves together with the poses (these are the ascertained geometric transformations to fit a depth image into a TSD; see also below) of the handpiece and provides the data of the overall model as a virtual image from the perspective of the previous depth image. The calculation of the translation vector and the rotation matrix (i.e. the registration) to "fill" a 3D measurement data set recorded with the handpiece happens with the aid of the ICP method (Iterative Closest Point Algorithm; see also: Russinkiewicz and Levoy, "Efficient variants of the iterative closest point algorithm", 2001).

In the ICP method, a rotation and a translatory movement (geometric transformation) are calculated in several iterations, starting from two point clouds. It is thereby possible to move one of the point clouds to the position of the other, so that the points of one point cloud lie as close as possible to the points of the other. To determine whether the points of a point cloud lie close to the points of another point cloud, for every point of a point cloud the corresponding point of the other point cloud is sought with the aid of a 2D depth image, provided this point is present and can be found. Thereby, pairs of points are generated. The distance between these point pairs is reduced by the ICP method in every iteration as much as possible.

In a sample system with two cameras and one projector three possible sources of data are available, called A, B, and C in this example. Data source A is in this case a (stereometric) camera-camera system with at least two cameras which provide depth information in the stereometric method of surveying surfaces familiar from the state of the art. Data source B is a camera-projector system with a first camera (for instance the left) and a projector which projects a pattern. In this system the distortion of an acquired pattern compared with a recorded pattern is measured. This can take place analogously to a stereometric system, for example by means of disparities between the recorded and acquired or projected patterns. Data source C operates analogously to data source B with the difference that a second camera, which is different than the first camera, furnishes the depth information relating to the projector. If more than the two cameras necessary for a stereometric system are provided for the handpiece, the number of available data sources increases automatically. For data sources A and B, the utilized camera coordinate system corresponds to the camera coordinate system of the first camera in each case, for data source C it is the projector coordinate system.

For every depth image from the various data sources a "confidence" image is recorded. In this case, the "confidence" image contains a quality information assigned every pixel of a depth image. This quality information conveys how small a calculated error of the depth information is. The calculation of the depth images takes place sequentially but based on the same camera images, so that the point in time of the recording and therefore the position of the handpiece is identical for all three sources. The position and orientation of the three systems with regard to each other is constant and is calculated during calibration. The actual merging of data from the various data sources takes place through a volume integration in a TSDF ("Truncated Signed Distance Function"), a special kind of notation for three-dimensional information.

In the state of the art, 3D scanners use either one or more physical cameras, in order to obtain two-dimensional data (usually two or more two-dimensional images) from one or more different perspectives, and reconstruct three-dimensional information from the two-dimensional images or also from parts of these. The reconstructed three-dimensional information is then used to register an image or a part thereof against a different image or part thereof ("frame to frame registration").

In contrast, according to a preferred application of the invention, initial three-dimensional information is first gained from two-dimensional images which are acquired with at least one physical camera. Then, three-dimensional data is calculated (reconstructed or "projected back" from the three-dimensional data) from the global model by means of a virtual camera. In doing so, no two-dimensional data is provided by the virtual camera, but rather three-dimensional data which stem directly from the global model. This three-dimensional data need not be the same in its spatial extent (with regard to the object) as the three-dimensional data, which is gained from the two-dimensional images of the physical camera. Then, the three-dimensional data from the physical camera is registered against the three-dimensional data from the virtual camera ("frame to model/global registration"). Since the global model always contains the entirety of the already compiled three-dimensional surface information, this kind of registration is always more accurate than registrations such as they are known from the state of the art.

Hereafter, the sample process described above will be summarized again:
  generating at least one two-dimensional image (first image set) by means of a physical camera
  constructing initial three-dimensional data from the first image set
  generating second three-dimensional data from the global model by means of the virtual camera
  determining correspondences (for instance by means of the ICP method)
  determining the geometric transformation (which corresponds to the camera movement or camera pose)
  updating the global model
  if required, generation of at least one new two-dimensional image by means of the physical camera, preferably from a new physical position of the physical camera.

According to the invention, the virtual three-dimensional surface geometry of the object to be captured is recorded in a TSDF ("truncated signed distance function"). At discrete coordinates (grid) within a defined volume, the TSDF provides the distance along a defined (coordinate) axis to the next surface. The algebraic sign of the function value or distance value provides information on whether this coordinate of the defined volume lies on the axis in front of or behind the surface. The discrete coordinates of the defined volume are also called voxels. Preferably, the voxels are equidistant. The actual surface is given implicitly by the TSDF and is situated at the positions, at which the function has the value zero. To precisely determine the surface it is sufficient to know the values of voxels which lie near the actual surface. Therefore, starting with a defined maximum value, a voxel is marked as "distant." Thus, the values which the function can assume are truncated. The size of the grid is preferably chosen to be large enough to contain the captured surface; ideally, a buffer will be included, for instance to compensate for sub-optimal positioning of the surface within the grid. The total number of grid points hereby influences the magnitude of the required computing resources. In principle, the required resources become larger for larger grids, or in other words, the scan process becomes slower for a larger grid if resources remain constant.

Aside from distance values, additional data, for instance pertaining to the quality of the distance value, can also be recorded in the voxels.

To integrate new data from newly acquired depth images into the model, the position of the scanner (the physical camera or cameras) relative to the grid must be known. Each voxel is tested, whether it is impacted by the new measurement, in which case its value can be corrected with the new data.

As also described by R. A. Newcombe et al. in "Kinectfusion: Real-time dense surface mapping and tracking" (ISMAR, 2011), the TSDF update works in a grid-oriented manner. Therefore it is especially suitable to be run by a processor working in parallel, especially a graphics processor (GPU).

The new depth data is integrated into the model by performing the following operations for every grid point or for every voxel independently of one another:
1. determining the voxel position from the point of view of the (virtual) camera
2. testing to determine with which pixel in the depth image a (certain) voxel in the TSDF corresponds
3. integrating the new distance information if a correspondence has been determined for a certain voxel in the depth image and the depth value is valid.

Since the cone of view of the scanner is generally smaller than the object to be captured, Step 3 is usually not performed for a majority of the voxels, because they lie outside of the cone of vision of the scanner and there is therefore no new data for these voxels.

If a distance to the surface which is larger than the defined maximum value is determined for a voxel, the voxel lies in a distant position in empty space according to the current measurement ("empty space update"). If the value of the distance is smaller than the maximum value, then it lies near the measured surface ("near surface update"). Otherwise, the value lies well in the negative range (smaller than a negative maximum) and the voxel is concealed and far behind the measured surface and should not be updated. In this manner, two different types of updates can be distinguished, depending on distance.

The type of update is influenced by other factors, according to the preferred implementation of the process. The state of the voxel prior to the update (for example, resulting from a previous iteration), in particular, is a factor. Thus, voxels which were marked in the previous iteration as lying in empty space can, for example, be treated as "empty" up to a specified number of contrary updates. On the basis of a combination of criteria, for instance voxel status and new values, different strategies are chosen for the given situation in order to improve the quality and accuracy of the distance value or at a minimum to avoid lowering them with conflicting data.

Generally, the number of updates is counted, preferably for each voxel, and recorded in the voxel. This number is a weight of the voxel. The number increases for iterations, in which a surface was recognized, remains the same, if the voxel was not updated, and decreases, if the voxel was recognized as empty ("empty space"). The number can therefore also be negative.

If several data sources are used (as described above), their depth images can each be integrated separately, taking into account the different camera coordinate systems and different camera parameters. A simultaneous measurement with different systems is integrated image by image, the same as different measurements from different perspectives. Ideally, the values from all systems will have the same quality. Otherwise, the data can be used to not close or improve yet measured or insufficiently measured sections of the surface, while well-captured areas of the model remain unchanged.

Which and how many sources are analyzed per iteration is in principle irrelevant for the TSDF; analyzing all available data sources (for instance first camera and second camera, first camera and projector, projector and second camera) is not, however, always practical:

When using all data sources simultaneously, the computational effort for the update of the TSDF is multiplied, and the attainable image rate decreases considerably. The additional data from camera-projector data sources usually only provide little additional value and primarily help to access areas that are difficult for stereo systems (first camera and second camera) to reach.

Depending on the situation and system performance, different preferable strategies are possible:

If the maximum image rate is to be achieved, analysis is preferably limited to one data source per iteration. Using a stereo system is particularly preferable.

Additionally, sporadically (for instance every $5^{th}$ frame), one of the two camera-projector systems can alternatingly be analyzed.

In addition or alternatively, the activation of further data sources can ensue automatically. If the scanner is largely stationary, for instance, or only moves very slowly, a lower image rate can, for example, be tolerated.

Furthermore, it is possible that with especially powerful computers, data processing takes place faster than data acquisition itself, which can for example be limited by means of the image rate of the employed cameras.

Deciding which sources should be used can also be done on the basis of model and position information, which can, for example, be gained by means of position sensors. If for example the content of a model area remains full of holes over multiple measurements, then an attempt can be made to fill it with camera-projector data. Positional information of the scanner or the cameras and/or projector, respectively, which is situated in the scanner, can be helpful, particularly when deciding which camera-projector data source is especially useful.

By means of the respective value of the weight of a voxel (weighting factor), three different voxel states can be differentiated for each individual voxel:

If the weighting factor is zero, the voxel is considered "unseen."

If the weighting factor is greater than zero, the voxel is considered to be "near surface."

If the weighting factor is less than zero, the voxel is considered to be "empty space."

Figure 1:
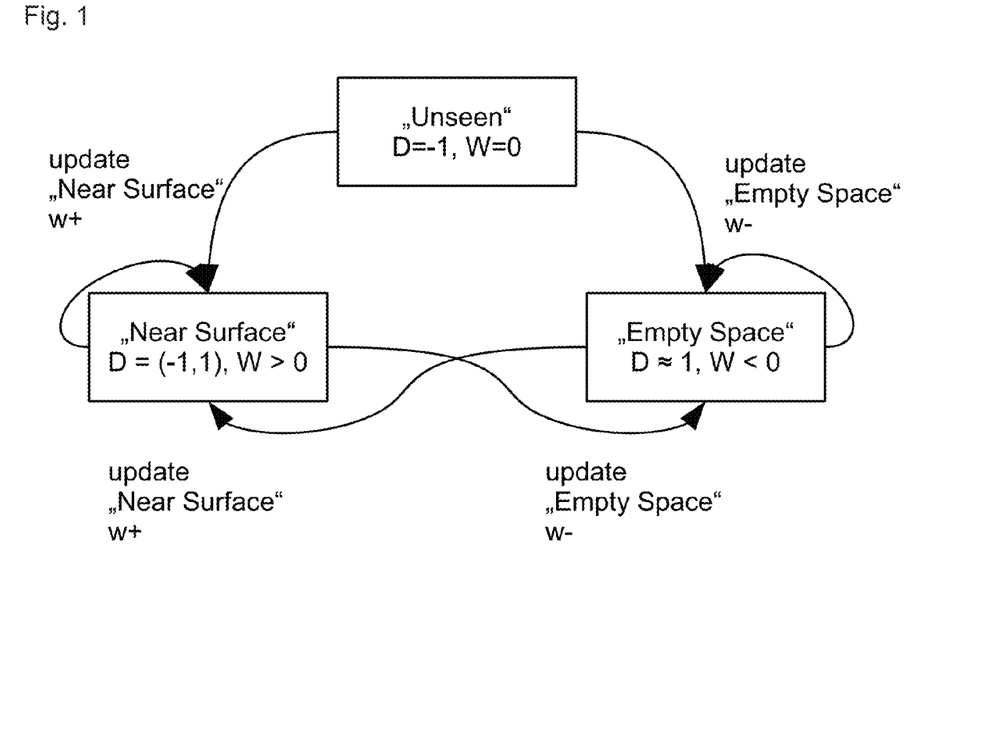
FIG. 1 a diagram for changing the states of voxels within a TSDF.

Compare also FIG. 1, which outlines how the voxel states are treated at "near surface" and "empty space" updates and when they change.

Before the first measurement, all values in the grid are unknown (voxel state: "unseen") and immediately upon the first update, receive a voxel state, a distance value and a weighting factor from the respective update.

If a voxel lies near an assumed surface (voxel state: "near surface"), and a new update confirms this assumption, then the new distance value is determined from the original distance value and the measured distance value. The weighting factor (voxel weight) then rises.

An "empty space" update of a voxel marked as being "near surface" therefore contradicts the weighting factor and state of this voxel, and therefore the weighting factor decreases. This can change the state of the voxel to "empty space," in which case the position value thus far recorded in the voxel will be overwritten with the maximum value.

Conversely, a voxel marked as empty (voxel state: "empty space") is assigned a weighting factor further in the negative range.

"Near surface" updates raise the weighting factor. This can lead to a change in state from "empty space" to "near surface." The maximum value thus far recorded in the voxel is thereby replaced by the distance value.

The accuracy of the measured data in the depth images is not entirely constant. The expected accuracy decreases, if the surface is not measured perpendicularly, but at a flat angle to the line of sight of the camera. At problematic spots, more measurements are necessary and good measurements are to be given preference, in order to create a sufficiently precise model.

To account for this characteristic of the scanner and better evaluate the validity of an individual measurement for the model, the weight of a voxel can, according to a preferred further stage of the invention, not only be used as a simple counter.

Depending on the evaluation of the quality/accuracy the current measurement is assigned a greater or lesser weight. The lower this value, the lower the influence on the distance value in the voxel and the lower the weighting factor of the voxel is raised. Thus areas that, for example, were previously only captured under poor conditions, can be improved through a small number of good measurements.

According to a preferred implementation of the invention, the weighting factor can be calculated from the cosine of the angle between the surface normal of the depth image and the direction of the point of view (angle of incidence). The surface normal of the depth image hereby corresponds to a normal to the surface captured by the depth image.

The weighting factor decreases in value accordingly, the flatter the angle at which the line of sight meets the surface. The surface normals of the depth image are already generated through the ICP method (during registration) and are available for the TSDF updates.

This intelligent weighting can be expanded, for example to take into account additional quality criteria of the depth images (for example from the "confidence" image).

The described process for weighting is preferably used in conjunction with the process according to the invention at hand, but it can also be used independently thereof.

The cliff approach for closing holes in the model, presented by S. F. Frisken and R. N. Perry in "Efficient estimation of 3D Euclidean distance fields from 2D range images" (Proceedings of the IEEE Symposium on Volume Visualization and Graphics), can also be used in a supplementary manner. To this end a surface is interpolated along the lines of sight at larger "steps" between adjacent values in the depth image, and the corresponding distance values are generated for the grid, in order to fill unknown areas. These interpolated distances are in turn overwritten by measured values without further consideration of the interpolated values.

According to a preferred further development of the invention, an additional smaller grid can be generated together with the TSDF. The number of grid points at the edges of the smaller grid is reduced by a defined factor, and can for example have a value of 8 or 16, in particular $2^n$. The smaller grids are each elements of the grid of the TSDF and are preferably cubes (bricks) which are composed of several voxels (for example 8×8×8, 16×16×16) in the TSDF grid. It can be specified for a brick, whether this cube could contain a surface. Should the brick only contain voxels with the voxel states "empty space" and "unseen," then the brick is marked as empty. This information can be used to accelerate the calculation of the surface, by being able to skip empty sections quickly without having to test every individual voxel.

Figure 2:
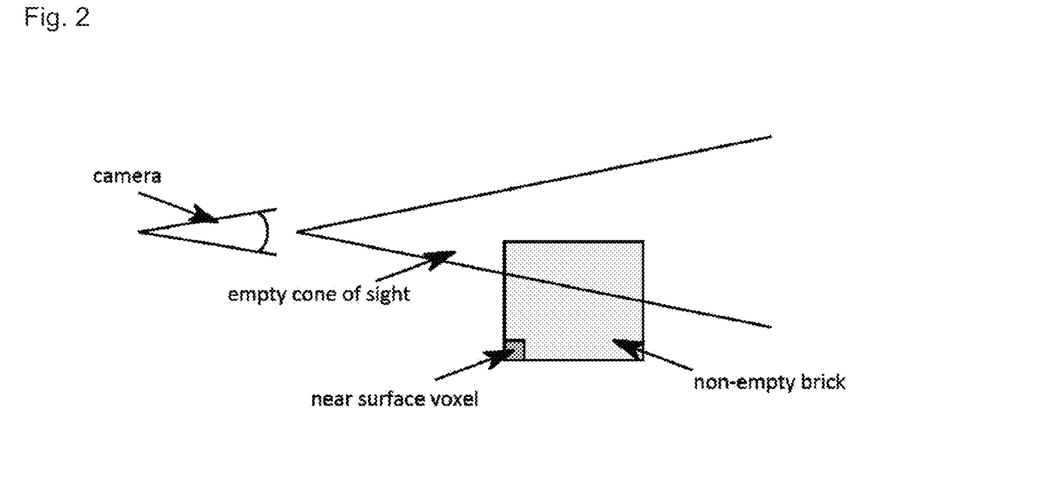

To save time and computational costs, only bricks within the cone of sight are updated in the course of the TSDF update. For bricks outside this area, no change is to be expected since the voxels corresponding to the bricks do not change, either ("empty space skipping"). After all voxels of a brick within the cone of sight have been updated, it is determined whether one or more voxels are near a surface. If this is the case, it is noted within the brick that it contains a surface. To this end all voxels of the brick are analyzed, even those that lie outside the cone of sight but belong to a brick within the cone of sight. Compare also FIG. 2.

Subdividing into bricks allows for the possibility of examining a coarse topology of the global model very quickly even during the process of scanning. It is therefore possible to find surfaces that are not part of the object to be captured and estimate their size. If, for example, the object to be captured is the arch of a jaw, an inadvertently captured tongue can be recognized. For this purpose, all bricks which are marked as containing a surface are consolidated into bundles. All bundles of surface bricks that are not directly connected with the largest bundle can be assumed by the model to be isolated fragments.

The fragments can, according to a preferred further development of the invention, be deleted, if appropriate after further testing of their size, by resetting the bricks of the isolated bundles and their voxels. With minor computational expense fragments, for instance of a tongue, cheek, and/or impurities in the glass cover, can be recognized and eliminated.

As previously described, it is envisaged that in the TSDF, only distance values with a maximum value in front of and behind the supposed surface should be dealt with. This however leads to the risk of falsifying another surface lying nearby in the background (such as the opposite sides of an incisor). At edges, in particular, snowdrift-like artifacts are thereby generated.

To recognize this case, the orientation of the measured surface in the depth image (the surface normal) can be compared with the approximate orientation of the surface recorded in the TSDF at the position of the voxel that is to be processed. See also FIG. 3.

Figure 3:
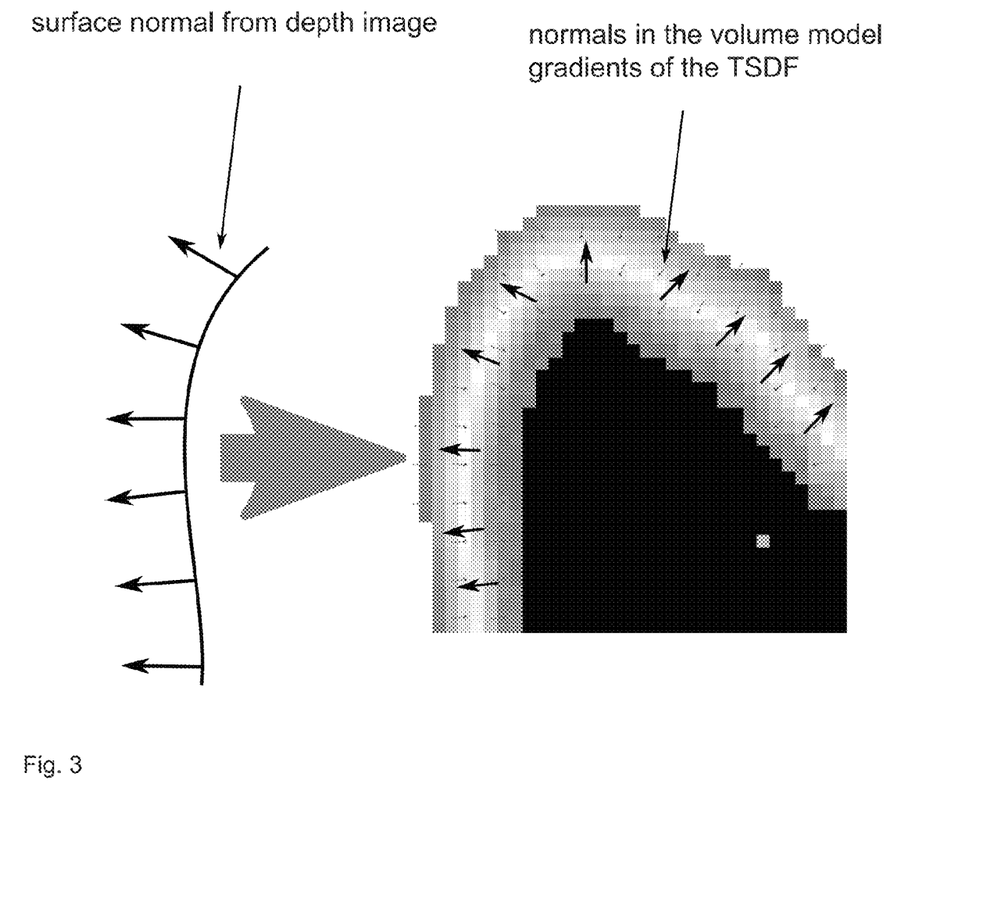

This comparison can essentially lead to three different situations:
1. Update from the front: The surface normals in the depth image and in the model are largely aligned. The measured distance value updates the distance value present in the voxel.
2. Update from the back: The surface normals in the depth image and in the model are largely oppositely aligned. The new distance value would falsify the distance value present in the voxel. An additional (facing) surface or a facing surface section can possibly be assumed.
3. Ambiguous update: The surfaces lie slanted toward one another or have only been captured to a small degree or not at all. In this case the quality-dependent weighting factor of the voxel can, for example, be reduced.

Depending on the situation, the influence of the new data point on the distance value of the voxel can now be determined with various weighting functions. For reverse and equivocal cases, the quality value is reduced by the resulting weight instead of raised as for updates from the front.

The weighting factor for updates from the front is essentially 1 for good correlations and drops in a linear manner with the cosine of the angle of incidence $\alpha$ down to 0 at the threshold value of $\cos \alpha = -\delta$. Worse correlations are "trusted" less; therefore only a minor influence on the distance value is desired.

$$\cos\alpha \epsilon [-1 \ldots -\delta] \to \omega_{front} = \frac{(-1)(\delta + \cos\alpha)}{1-\delta} \quad \text{(Formula 1)}$$

An update from the rear should not be generally excluded, because some fragments could then not be updated and therefore permanently falsify the captured surface. Instead, the new (measured) distance value is only added to voxels which lie less than a threshold value $-\delta_{dist}$ behind the surface according to its (existing) distance value. The further the voxel lies behind the surface, the less the new value is trusted.

$$\cos \alpha \epsilon[-1 \ldots -\delta] \to \omega_{back} = \max(0, \cos \alpha (-\delta_{dist} - d_{old})(1-|d_{new}|)) \quad \text{(Formula 2)}$$

Figure 4:
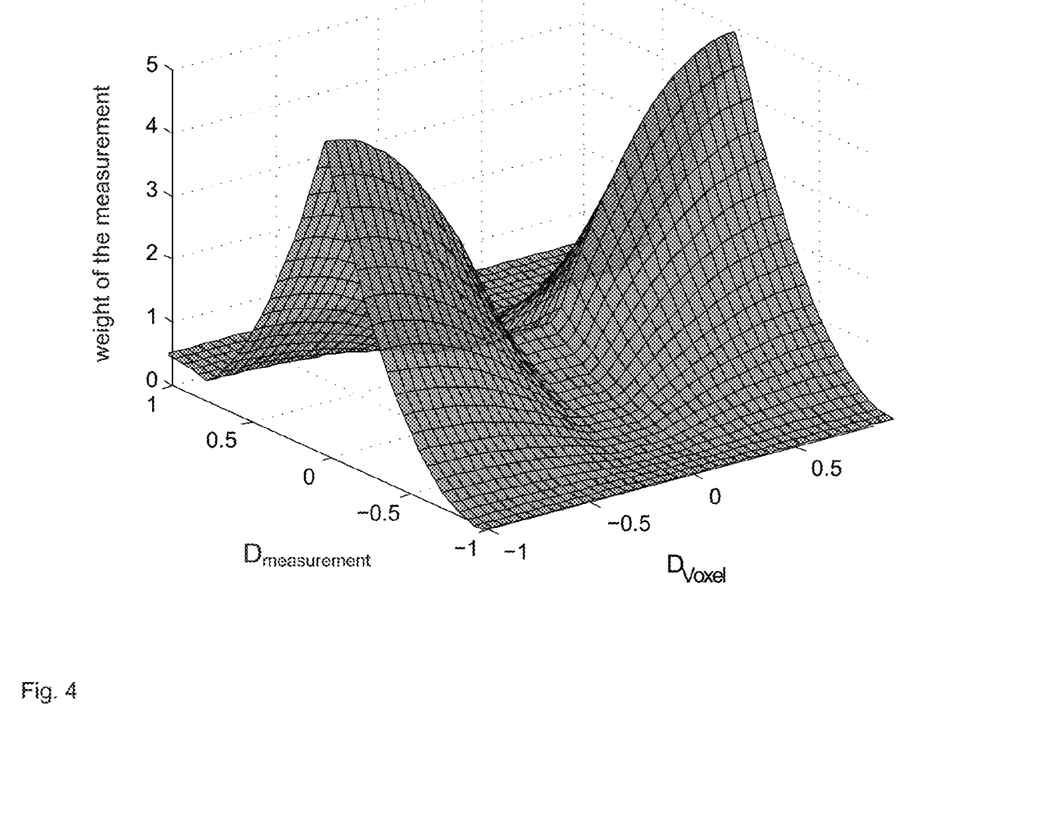

In ambiguous cases, a weighting factor that dampens snowdrift-like distortions without negatively impacting other parts of the captured surface can only be determined by means of the combination of the distance value of a voxel and the new distance value. See also FIG. 4. The function $w=f(D_{alt}; D_{neu})$ depicted therein is empirically selected in such a manner that it is symmetrical in the vicinity of the surface and provides sufficiently high weighting factors that the distance value is, as much as is possible, not falsified. By the vicinity of the surface we mean that both distance values (measured and pre-existent) are close to zero.

If a new, very high distance value is measured for a voxel with a low recorded distance value, it is probably a measurement error. However, it is not advisable to prohibit updates completely in this case, since measurement errors from prior measurements which, for lack of data, have not yet been recognized as such, and measurement errors due to foreign objects, for instance a tongue, can then no longer be corrected. Therefore, it is advisable that voxels with high weighting factors can still be influenced in this manner.

The object to be captured, for instance the arch of a jaw, can be assumed to be static during the scanning process if no changes are made during the scanning process, in particular, if no teeth or prosthetics are introduced or removed. Unwanted objects that are seen by the scanner, such as a tongue, cheek, blood, saliva, and foreign objects, are generally movable. This assumption can be used to improve the performance, quality and comfort of the scanning procedure considerably. Assuming that the scan begins on a static object, for instance a tooth, the captured (virtual) surface does not shift within the global model or the grid of the TSDF, respectively.

It is therefore impossible that (undesired) captured surfaces are captured in areas in which the scanner is located or has been located.

During the update of the TSDF sections (voxels) which lie within a (defined) scanner volume can without further ado be permanently marked as empty ("empty space"). Undesired surfaces and artifacts can thus be "erased" by moving the scanner in real space to a position where a flawed captured surface is recorded in the corresponding virtual space. In implementation of the process used as an example, a previously captured tongue can, for example, be pushed aside with the scanner head. These areas can then be permanently excluded from the updating process. This decreases the computational cost, and also prevents later appearances of new artifacts in this area.

Figure 5:
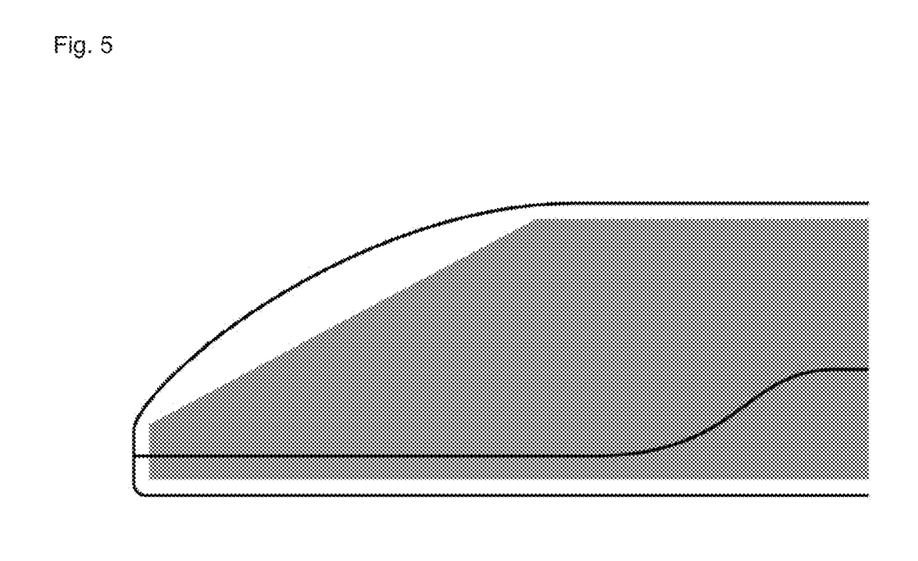

Ideally, the defined scanner volume (modeled volume) will be identical with the volume of the scanner: in practice it should be chosen to be slightly (for instance 5%) smaller. In some places, through simplification of the surface, it can readily it can be considerably smaller than the actual measurements (see also FIG. 5). If the modeled volume is exactly the same size or larger, correctly surveyed dental surfaces could, under certain circumstances, also be deleted, for instance if the scanner is placed there.

According to a preferred further development of the invention, voxels in the erased area are merely assigned a very high negative weighting factor, such as −30000, rather than a binary attribute "erased"/"not erased."

In some situations it can be useful to reduce the weighting values of the voxels in order to be able to update them more quickly. No longer present surfaces (for instance after preparation of the teeth) disappear more quickly in the course of new updates if their weighting factors are small. In "erased" areas a new surface can only be formed after resetting the weighting values, i.e. reduced the "erased" mark or resetting the recorded weighting value, for instance to "unseen."

According to various preferred implementations of the process, resetting can, for instance, take place in one of the following described ways:
  All weighting factors higher than a threshold weighting factor can be set to the weighting factor threshold
  If the proportions of the weighting factors among the voxels should be preserved, the weights can also be scaled by a factor (for instance with the factor 0.5).
  Any other function can also be applied to the weighting factors, as long as this function is applied equally to all weighting factors in the TSDF.
Various combinations of these variants are also conceivable.

Resetting the weighting factors can, for example, take place during a pause mode, or also before a TSDF which was loaded from a storage medium is updated. This can, where applicable, (always) take place automatically as an available TSDF is loaded or retrieved.

Several concrete sample applications of the invention for resetting and/or erasing, which can preferably be implemented with the invention at hand, but also be implemented independently thereof, will again be briefly summarized and explained below.
  An already surveyed jaw is updated following a change, such as an (additional) preparation or also implantation of prosthetic elements, such as a dental crown.
  Part of the model has been recorded incorrectly. There could, for instance, be undesired tongue, cheek, lip, and/or gum fragments, or fragments from dental tools such as mirrors, for example, in the TSDF, which make precise data collection considerably more difficult.
  Whenever a scan is aborted (i.e. before its resumption), the weighting factor can automatically be reduced, for instance to 50%.
  Automatically resetting when a scan is aborted is also sensible when the user cleans the scanner or the tooth (for instance when removing saliva) and wishes to rescan the corresponding area. In this case, automatically resetting helps to eliminate measurement errors caused by saliva in a simpler manner, without the user having to remember to reset.

In a preferred implementation of the invention it is possible for the user to receive an indication during resetting, for example by colorizing a visualization of the TSDF which is easy for the user to grasp, which informs of the reset. Analogously, (newly) updated areas can subsequently also be visualized, for instance through a change in color.

Alternatively, resetting can also occur without the user receiving an indication thereof.

According to an additional or alternative implementation of the invention, only certain regions of the model (within the visualized TSDF) can also be selected by the user, for example through manual interaction with a mouse or a touchscreen. It is thereby possible to treat the voxels of the marked area separately. In doing so, the weighting values of the voxels in the chosen area are reset using one of the methods described above while the weighting values of the voxels outside of the chosen area remain the same or are reduced by a different factor or set to a different value.

It is also conceivable that the weighting values of the voxels outside of the marked area should be set to a greater value so that, for example, these can no longer change and therefore no longer be negatively influence by poor measurements, for instance those caused by saliva.

In a further preferred advantageous implementation of the invention, a so-called resumption mode is envisaged.

To this end, first the geometric transformation (also called pose) is recorded in the originally captured TSDF for each (successful) update.

After finishing (or pausing) the scan, a new depth image is gained in resumption mode. Then an attempt is made to register the new depth image in the existing TSDF using the recorded poses. The pose in which the new distance values in the voxels correspond best with the existing distance values is then selected. For this selection, the square error can be used (see also: "least squares method," C. F. Gauss).

In a further development of the invention the bricks described above can also be used in resumption mode to optimize performance.

This can take place in the following steps in a sample implementation of the invention:
1. Loading an available TSDF from a storage medium;
2. Providing the bricks of the existing TSDF;
3. Assigning the attribute "near surface brick" to all bricks in which at least one voxel with the attribute "near surface" is present;
4. Loading available poses to the loaded TSDF;
5. Capturing a new depth image;
6. Applying the available poses to the new depth image (transformation of the new depth image by means of the available poses for testing purposes):
   a) Verifying for each transformed point of the depth image whether the point lies within a brick with the attribute "near surface brick" due to the employed pose, and labeling of the point;
   b) Counting all labeled points in the depth image for each pose;
7. Selection of the pose which leads to the most labeled points;
8. Generation of an artificial depth image from the TSDF by means of the selected pose;
9. Application of an ICP method to the new depth image and the artificial depth image;
10. Verification whether the ICP method from Step 9 leads to a successful registration;
11. If Step 10) provides positive feedback, updating of the existing TSDF by means of the new depth image and the pose gained in Step 10 by means of the ICP method;

12. If Step 10) provides negative feedback, repetition of the steps beginning with Step 5).

Step 4) can also take place independently of resumption mode, for instance directly when (initially) recording the available TSDF. In this case, the attribute of the bricks is loaded directly with the bricks in Step 2) and Step 3) can be omitted.

The generation of an artificial depth image in Step 8 can be performed, for example, by creating 2.5-dimensional image of the surface recorded in the TSDF from the TSDF by means of the ray-casting method from the "perspective" of the selected pose. Compare also: A. Neubauer et al. "Cell-based first-hit ray casting", Proceedings of the Symposium on Data Visualisation 2002, pages 77ff.

Figure 6:
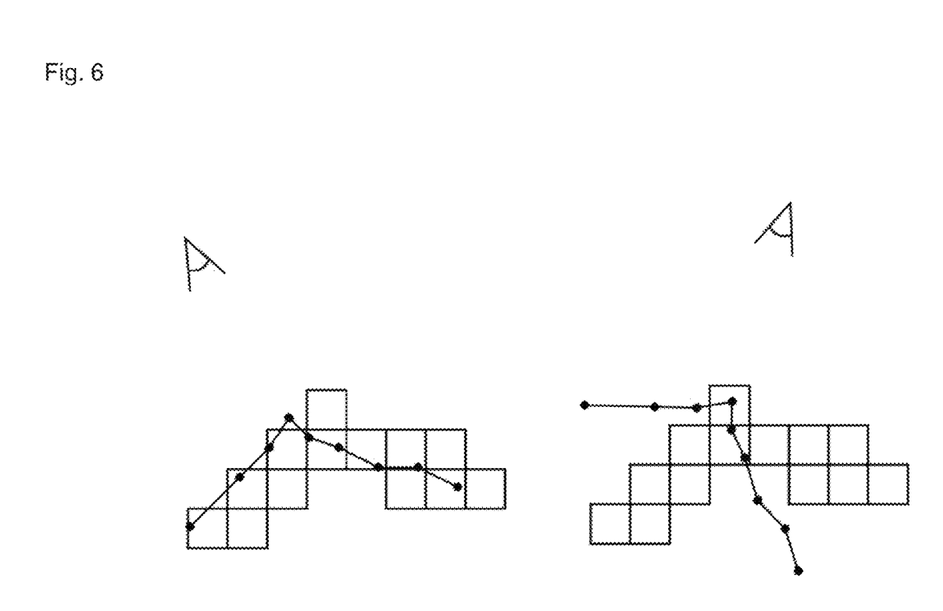

Steps 6), 6.a) and 6.b) are again illustrated further in FIG. 6.

In a further development of the invention, so-called artificial poses can also be used in steps 6) through 11) along with poses that are loaded with the TSDF (see also Step 4). Artificial poses are created by applying any desired translations and rotations. This has the advantage of increasing the flexibility in resumption mode. For instance, a scan can more easily be resumed following a 180° rotation of the scanner, for example in a scan of the entire jaw following an interruption at the incisors, if (at least) one artificial pose which has been rotated by 180° has been created.

Additionally or alternatively, additional information can be included when creating artificial poses and/or selecting a pose in Steps 6) through 10). Positional data from acceleration and rotation rate sensors, in particular, can provide indications on which of the recorded poses are suitable for the resumption. This data can also be used to vary the more suitable poses in a targeted manner (creation of artificial poses). The reliability of this data is, however, limited; it can also be contradictory if the patient should move.

As already described above, a user can be supported by indicators, in particular visual indicators. Therefore it is envisaged that in a preferred further development of the invention, the (complete) visualization of the TSDF will be furnished with such indicators.

As described above, each voxel of the TSDF contains a weighting function. This weighting factor can be used to color a visualization of the TSDF. Since the weighting factor is correlated directly with the quality (or the precision) of the distance values recorded in the voxels of the TSDF, the user can intuitively draw conclusions on the quality of the recorded data from colors linked to the weighting. From this, a direct and easily understood usage guide arises for the user, since "bad" areas will need to be scanned anew under certain circumstances.

These indicators can for example be color values, differing transparency, brightness and the like.

Additional preferred implementations of the invention are the subject of the remaining dependent claims.

The invention claimed is:

1. A method for capturing the three-dimensional surface geometry of objects, in which the following steps are performed:
   1) Loading an available truncated signed distance function (TSDF) from a storage medium;
   2) Capturing a new depth image;
   3) Loading available poses to the loaded TSDF;
   4) Applying the loaded poses to the loaded TSDF;
      a) Verifying for each point of the depth image which has been transformed by applying the loaded pose, whether the point has a first defined attribute due to the applied pose and, if applicable, labeling of the point;
      b) Counting all labeled points in the depth image for each pose;
   5) Preferred selection of the pose, which leads to the most labeled points;
   6) Generation of an artificial depth image from the TSDF by means of the selected pose;
   7) Application of an Iterative Closest Point Algorithm (ICP) method to the new depth image and the artificial depth image to gain a new pose;
   8) Verification of whether the ICP method from Step 7) leads to a successful registration;
   9) If Step 8) is successful, updating of the existing TSDF by means of the new depth image and the pose gained in Step 7);
   10) If Step 8) is unsuccessful, repetition of the steps beginning with Step 4).

2. The method according to claim 1, wherein the Step of:
3.1) Creation of artificial poses in addition to the existing poses, and loading of the artificial poses
is performed before Step 4), and by the creation of the artificial poses happening by means of the application of geometric operations to the existing poses.

3. The method according to claim 2, wherein the Step of:
1.1) Providing bricks to the loaded TSDF
follows after Step 1).

4. The method according to claim 3, wherein the Step of:
1.2 Determining which of the provided bricks fulfill a second defined attribute and marking of those bricks
follows after Step 1.1).

5. The method according to claim 4, wherein, if Step 1.2) has been completed, then the Step of:
4)a.1) For each point which has been transformed by applying the loaded pose, testing whether the point lies within a brick with the second defined attribute thanks to the applied pose, and marking the point if applicable
follows instead of Step 4)a).

6. The method according to claim 1, wherein the Step of:
1.1) Providing bricks to the loaded TSDF follows after Step 1).

7. The method according to claim 6, wherein the Step of:
1.2 Determining which of the provided bricks fulfill a second defined attribute and marking of those bricks follows after Step 1.1).

8. The method according to claim 7, wherein, if Step 1.2) has been completed, then the Step of:
4)a.1) For each point which has been transformed by applying the loaded pose, testing whether the point lies within a brick with the second defined attribute thanks to the applied pose, and marking the point if applicable
follows instead of Step 4)a).

9. The method according to claim 1, wherein the objects are any of teeth and/or intraoral structures.

* * * * *